United States Patent [19]

Nowatzki

[11] Patent Number: 5,302,359
[45] Date of Patent: Apr. 12, 1994

[54] DEODORIZING SYSTEM

[76] Inventor: Raymond L. Nowatzki, 2310 Rte. #63, Wayland, N.Y. 14572

[21] Appl. No.: 977,918

[22] Filed: Nov. 18, 1992

[51] Int. Cl.⁵ ................................................ A61L 9/00
[52] U.S. Cl. .................................... 422/306; 422/120; 422/123; 422/124; 261/DIG. 17; 261/27; 261/103; 261/106; 239/49
[58] Field of Search .................. 422/4, 5, 120, 123, 422/124, 305, 306; 239/49, 42; 261/DIG. 15, DIG. 17, DIG. 65, 27, 103, 106

[56] References Cited

U.S. PATENT DOCUMENTS

| | | | |
|---|---|---|---|
| 4,301,094 | 11/1981 | Baus | 261/103 |
| 4,383,951 | 5/1983 | Palson | 261/DIG. 17 |
| 4,601,886 | 7/1986 | Hudgins | 422/306 |
| 5,171,485 | 12/1992 | Ryan | 261/27 |

*Primary Examiner*—Robert J. Warden
*Assistant Examiner*—T. A. Trembley
*Attorney, Agent, or Firm*—Howard J. Greenwald

[57] ABSTRACT

An apparatus for dispensing odorant vapor into an air stream is disclosed. The apparatus contains a reservoir for containing a volatilizable liquid, a dispensing well, liquid moving means for withdrawing liquid from the reservoir and causing it to flow into the dispensing well, and switch means for activating the liquid moving means.

7 Claims, 4 Drawing Sheets

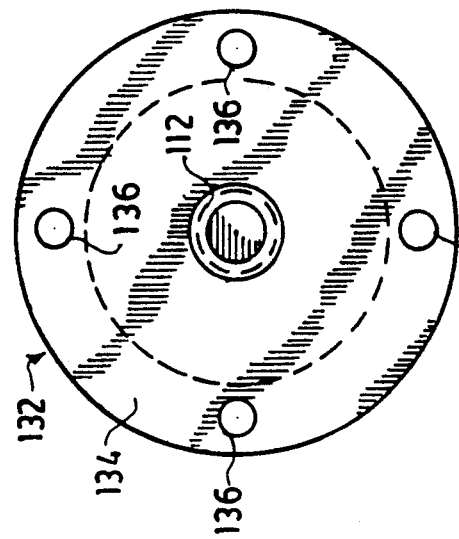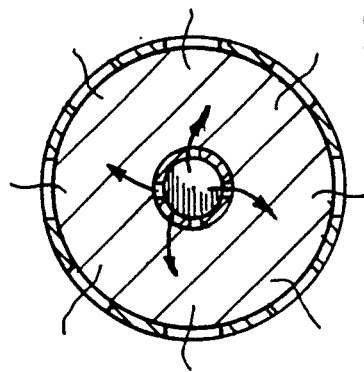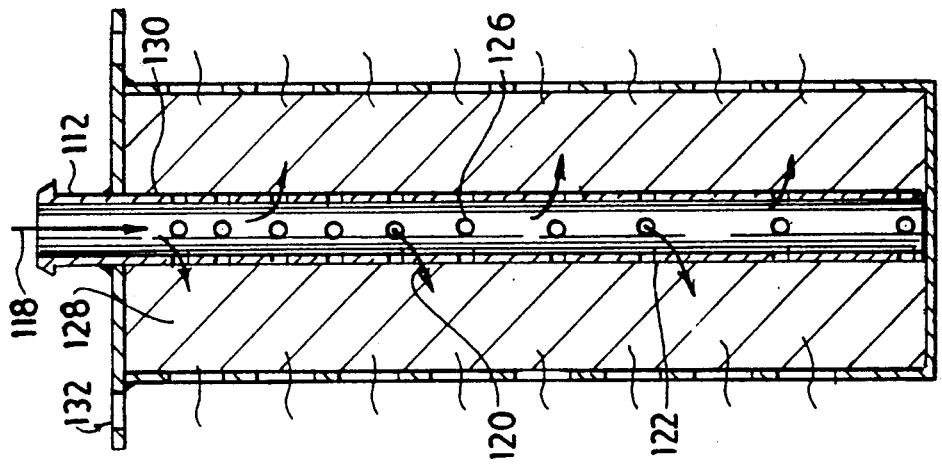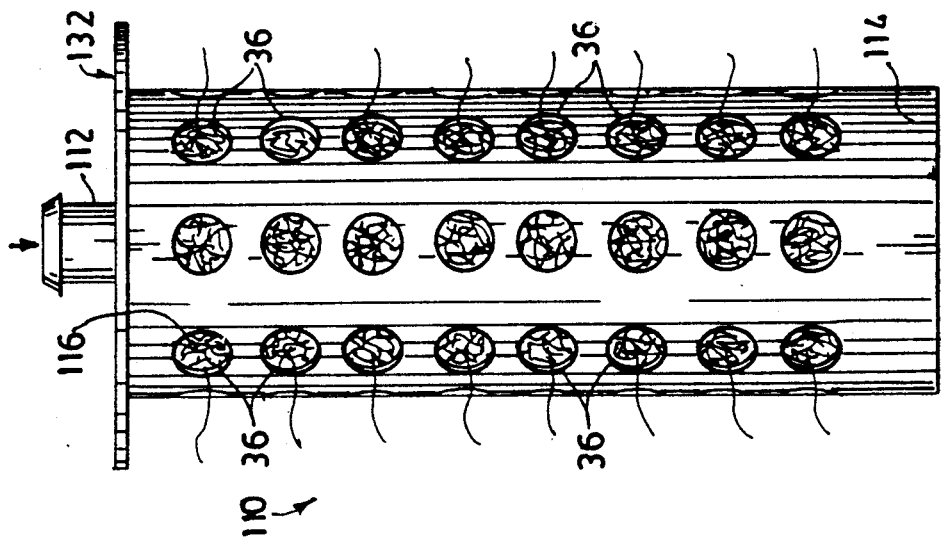

_5,302,359_

DEODORIZING SYSTEM

FIELD OF THE INVENTION

An apparatus for dispensing liquid deodorant into a air circulation system which contains a manually operated switch, a source of liquid deodorant, and a pump.

BACKGROUND OF THE INVENTION

Devices for dispensing deodorant into an air stream air stream are known to those skilled in the art. Thus, for example, U.S. Pat. No. 2,807,893 of Morey discloses a a dispenser 15 mounted in a clothes dryer. The dispenser is comprised of a container filled with deodorizing volatile liquid. When the clothes dryer is in operation, air generated by a blower in the dryer contacts the dispenser and volatilizes a portion of the liquid.

A somewhat similar system was described in U.S. Pat. No. 4,229,415 of Bryson. The Bryson patent discloses a portable dispenser 11 containing a basket 51 and posts 57 which, in combination, retain between them a series of envelopes 61 which contain an odorant to be dispensed. Air flowing past the envelopes 61 causes the volatilization of the odorant.

Another similar system was disclosed in U.S. Pat. No. 4,383,377 of Thomas W. Crafton. The device of the Crafton patent is a hot air hand dryer containing a container mounted in the intake grill; the container included openings allowing air flow through it. A stick or disk of vaporizable deodorant was disposed within the container, and the air flow through it caused vaporization of odorant.

U.S. Pat. No. 4,903,584 discloses a building air vent assembly containing a vent opening, a damper plate, a trough with an open side for receiving deodorant, and a deodorant sheet within such trough. When air flows through the vent, it passes over the deodorant sheet in the trough and partially vaporizes it.

To the best of applicant's knowledge, none of the prior art devices affords the user the flexibility of readily dispensing the amount of deodorant he or she desires only when so desired. The devices of U.S. Pat. Nos. 2,807,893, 4,383,377, and 4,903,584 function automatically when air is flowing through them and are not subject to a substantial amount of control and adjustment by a user. The device of U.S. Pat. No. 4,229,415 utilizes a deodorizing package which, to the best of applicant's knowledge, is not readily commercially available.

It is an object of this invention to provide a deodorizing system which utilizes volatile deodorant liquid.

It is another object of this invention to provide a deodorizing system which can be manually activated at any time, and to any extent desired, by a user.

It is another object of this invention to provide a deodorizing system which contains means for activating the system at one or more specified periods of time.

SUMMARY OF THE INVENTION

In accordance with this invention, there is provided a deodorizing system which contains a switch, a pump operatively connected to such switch, a reservoir containing liquid odorant, a dispenser, and means conveying at least a portion of such liquid odorant into the dispenser.

BRIEF DESCRIPTION OF THE DRAWINGS

The present invention will be more fully understood by reference to the following detailed description thereof, when read in conjunction with the attached drawings, wherein like reference numerals refer to like elements, and wherein:

FIG. 7 is a perspective view of a dispensing well which may be used in the deodorizing system of FIG. 1;

FIG. 8 is a sectional view of the core of the dispensing well of FIG. 7;

FIG. 9 is a top view of the cap of the dispensing well of FIG. 7; and

FIG. 10 is a top view of the core of the dispensing well of FIG. 8.

DESCRIPTION OF THE PREFERRED EMBODIMENTS

Figure 1:
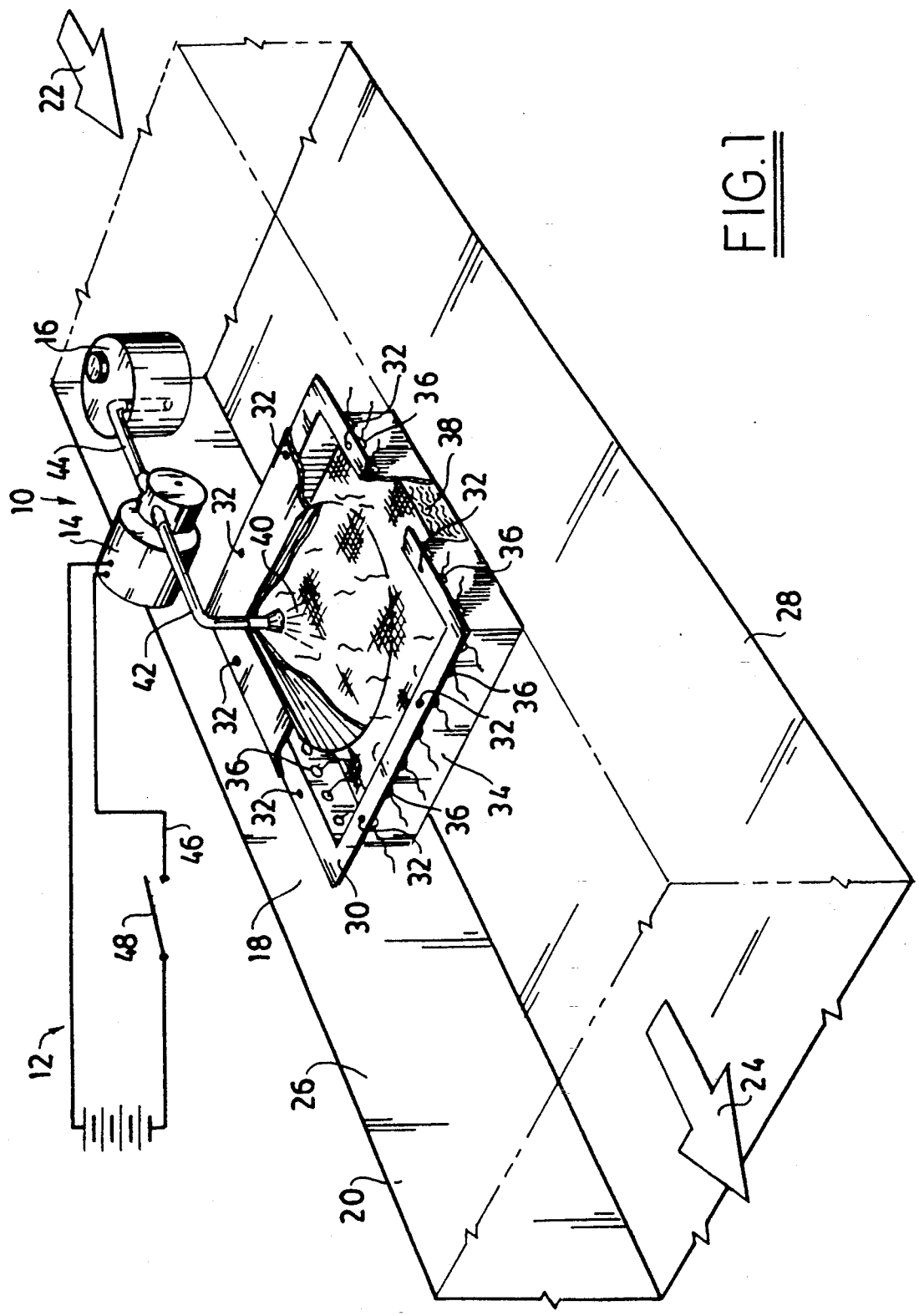
FIG. 1 is a partial top view of a preferred embodiment of applicant's system disposed within an air duct.

FIG. 1 illustrates one preferred embodiment, and means of using, applicant's deodorant dispensing system 10.

Referring to FIG. 1, it will be seen that dispensing system 10 is comprised of a switch 12, a pump 14, a reservoir 16, and a dispensing well 18. The unit 10 is partially disposed within ductwork 20. As air flows through ductwork 20 in the direction of arrows 22 and 24, it will pass, at least in part, around the sides of and underneath dispensing well 18.

Referring again to FIG. 1, and in the preferred embodiment illustrated therein, it will be seen that dispensing unit 10 may be disposed at any desired position within either the top surface 26 and/or a side surface 28 of ductwork 20. A suitable opening (not shown) is cut into one or more of the surfaces of the ductwork 20, and the dispenser 10 is placed into such opening so that flange 30 contacts a portion of the mating surface. Thereafter, by conventional means (such as sealant, a gasket, sheet metal screws through holes 32, etc.), the unit 18 may then be attached to the ductwork 20 in any desired position and location. When so attached, the bottom portion 34 of the dispensing well 18 will be disposed within ductwork 20. A multiplicity of orifices 36, which may appear on one or more of the sides of dispensing well 18, allows air within such dispensing well 18 to flow out into the ductwork 20.

Referring again to FIG. 1, it will be seen that dispensing well 18 preferred is comprised of absorbent material 38 which may contain deodorant liquid. The deodorant liquid 40 may be dispensed onto material 38 through pipe 42 when switch 12 is activated.

Any of the volatilizable liquid deodorants known to those skilled in the art may be used in the invention. Thus, by way of illustration and not limitation, one may use the malodor counteractant disclosed in U.S. Pat. No. 4,187,251, the hydrosylate of keratin material disclosed in U.S. Pat. No. 4,591,497, the cyclohexyl alcohol and ester derivatives disclosed in U.S. Pat. No. 4,622,221, and the like. It will be apparent to those skilled in the art that this list is merely illustrative and that many other liquid deodorizing compositions may be used in applicant's device.

The liquid deodorant which is pumped into dispensing well 18 is retained in the bottom of such well and, as it is vaporized, passes through the orifices 36 in the top of such well and into the ductwork 20 in gaseous form.

Reservoir 16 is provided with a supply of liquid deodorant 40 which may be periodically withdrawn therefrom by means of line 44. When switch 12 is activated, it causes vacuum pump 14 to pull deodorant liquid 40 from reservoir 16 to line 42 and thence into dispensing well 18.

Any pump means for withdrawing liquid from reservoir 16 may be used in applicant's invention. Thus, by way of illustration and not limitation, one may use any of the vacuum pumps described on pages A249 to A255 of the 1992-1993 "Fluid Power Handbook & Directory" (published by Hydraulics & Pneumatics magazine, 1100 Superior Avenue, Cleveland, Ohio). Thus, for example, one may use a reciprocating piston pump, a diaphragm pump, a rotary vane pump, a rotary screw pump, a lobed rotor pump, and the like. Other similar means also may be used.

The pump 14 is activated by switch 12. In the embodiment shown, when contacts 46 and 48 complete the electrical circuit, the pump 14 is activated, and deodorant fluid 40 is dispensed into dispensing well 18.

The user can control the amount of deodorant fluid dispensed by the length of time he causes contacts 44 and 46 to close switch circuit 12. In one embodiment, 44 and/or 46 are spring-loaded and are normally in an open position.

In another preferred embodiment, not shown, switch 12 is electrically connected to a timer means, not shown, which closes contacts 44 and 46 only at specified periods of time and/or only for specified periods of time. Thus, for example, any of the timers which are commercially available may be used as such means.

By way of illustration, and with reference to the Tandy Electronics catalog 7.0 (Tandy Electronics National Parts Division, 900 E. North Side Drive, Fort Worth, Tex.), one may use the solid state timers disclosed on pages 205-209 of such catalog. One or more of such timers may be used in conjunction with the switches disclosed at pages 192-204 of such catalog.

One or more of the components of system 10 may be made of metal. In one preferred embodiment, however, the dispensing well 18 and/or the reservoir 16 preferably consist essentially of plastic material.

Figure 2:
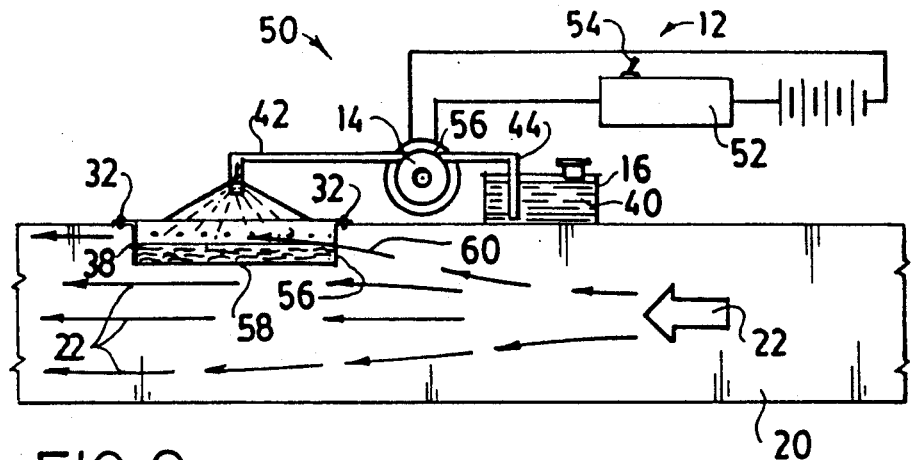
FIG. 2 is a side view of the system of FIG. 1 disposed within an air duct.

FIG. 2 is a side view of another preferred embodiment of applicant's invention. Referring to FIG. 2, it will be seen that dispensing device 50 is comprised of timer 52 which may be automatically operated and, alternatively, operated with manual switch 54. The activation of switch 54 will cause motor 56 to activate pump 14 and thereby cause deodorizing fluid 40 to flow into dispensing well 18.

In the embodiment depicted, air flow through ductwork 20 normally flows in the direction of arrows 22. Some of such air flows around the sides 54 and 56 and/or the bottom 58 of the housing of dispensing well 18. Some of such air, such as the air flowing in the direction of arrow 60, flows through one or more of the orifices 36 in the dispensing well.

Figure 3:
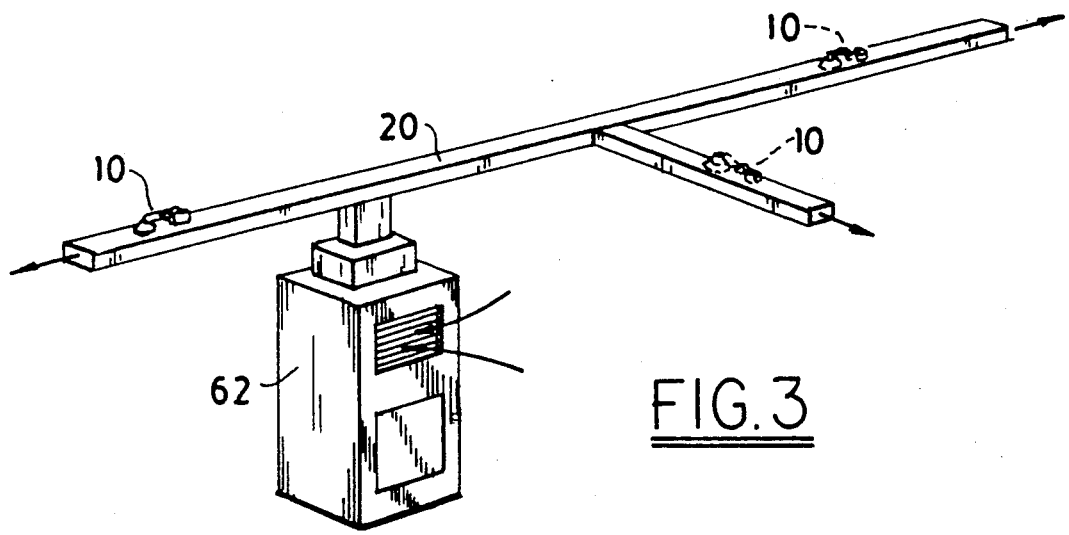
FIG. 3 is a perspective view of a furnace containing applicant's system connected to ductwork in a building.

FIG. 3 illustrates a heating system comprised of a furnace and/or central air conditioning system 62 connected to metal ductwork 20. By selectively locating one or more dispensing units 10 at various portions of the ductwork 20, one may provide selected branches of such ductwork with deodorizing capabilities (which may vary from unit 10 to unit 10) and allow separate control of such capabilities for each of such branches.

Figure 4:
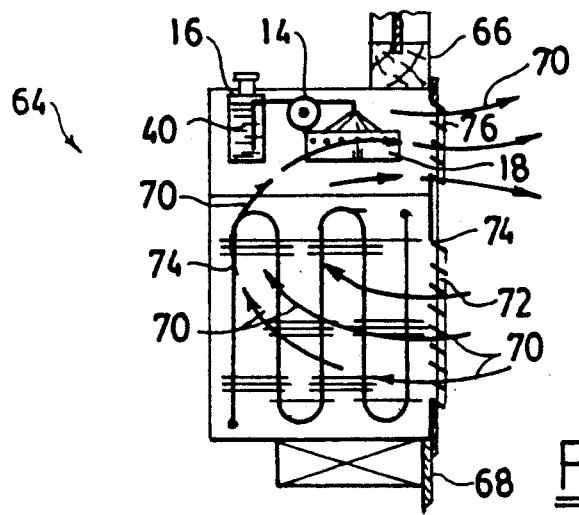
FIG. 4 is a sectional view of a window air conditioner containing the deodorizing system of FIG. 1.

FIG. 4 is a sectional view illustrating deodorant system 10 mounted within a window air conditioning unit 64. Substantially any air conditioning unit may be used with applicant's system 10. The particular unit illustrated in FIG. 4 is a Fedders window air conditioner described in publication No. 23-11-0723N-006 (Fedders Air Conditioning U.S.A., Inc., Effingham, Ill., 1988); and it is secured by window 66 and window sill 68.

Referring to FIG. 4, air travels in the direction of arrows 70 through sponge filter 72, through cooling coils 74, past and partially through dispensing well 18, and out through discharge port 76. The air flowing through the discharge port contains some gaseous deodorant particles.

Figure 5:
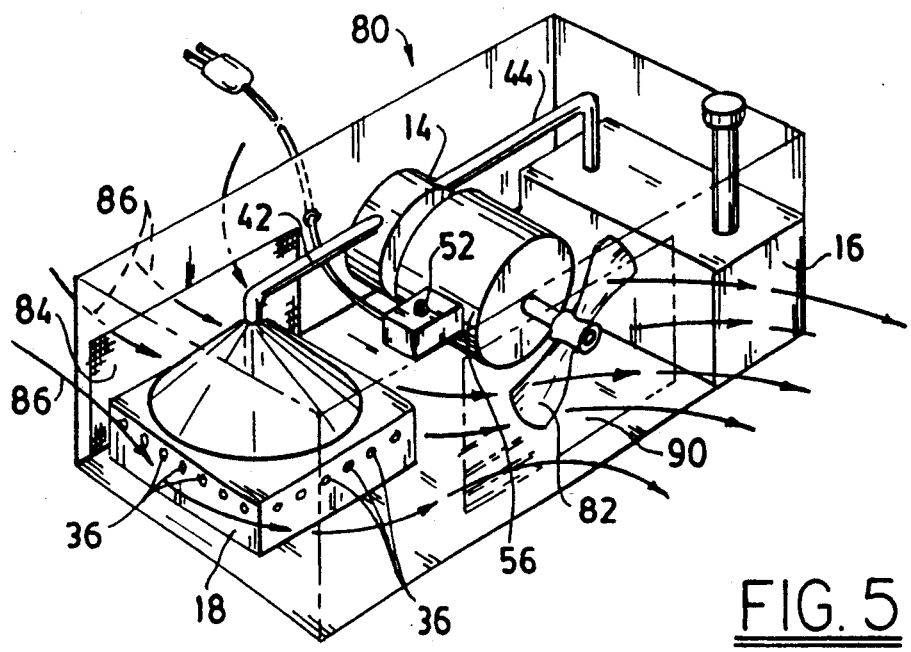
FIG. 5 is a perspective view of another preferred deodorizing system of applicant's invention.

FIG. 5 illustrates another preferred deodorant dispensing system 80. In this embodiment, motor 56 drives both the pump 14 and a fan 82. The operation of fan 82 causes air to flow through grill 84 in the direction of arrows 86 past, under, around, and/or through dispensing well 18 and, thereafter, out through grill 90.

Figure 6:
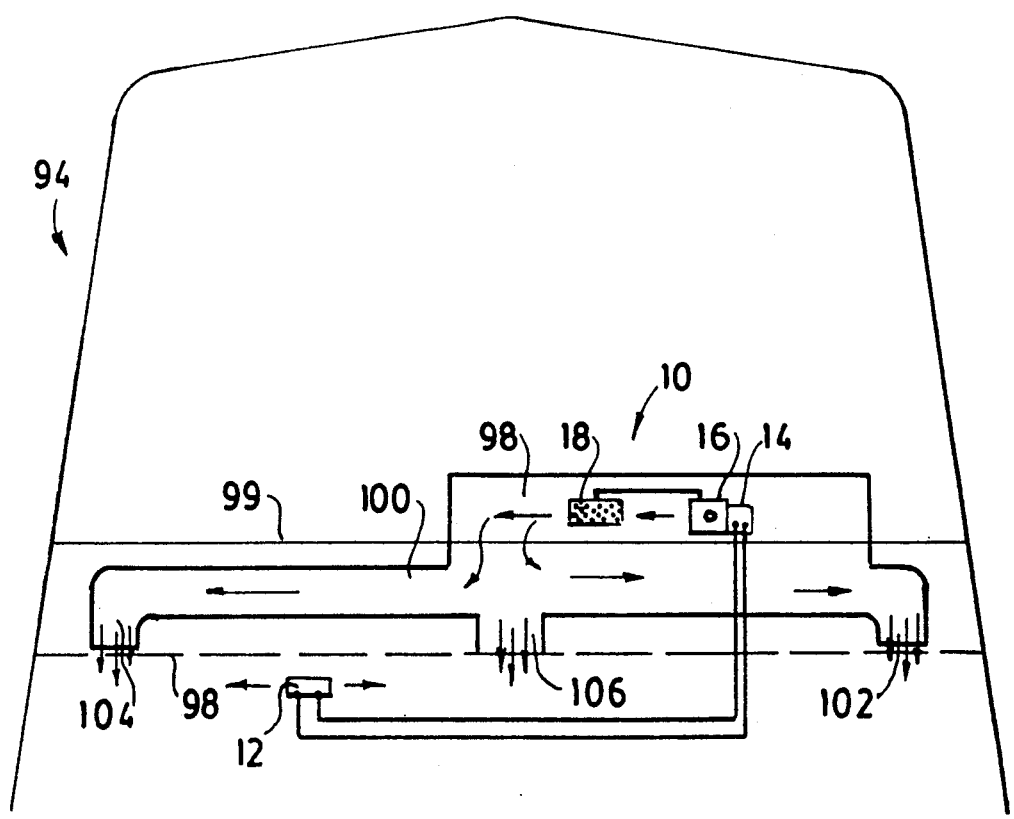
FIG. 6 is a schematic of one embodiment of applicant's deodorizing system installed in an automobile's ventilation system.

FIG. 6 is a top view, partially broken away, of an automobile 94. Referring to FIG. 6, switch may be located substantially anywhere in, on, or near dashboard 96. The deodorizing system 10 may be mounted in a ventilation system housing 98 in front of firewall 99 beneath the hood of the automobile. Air flowing into the ventilation system from the outside (not shown) passes around, under, and/or through dispensing well 18, and then it flows through ductwork 100 to interior vents 102, 104, and 106. As will be apparent to those skilled in the art, in this embodiment the system 10 may be operated manually, and/or with the use of a timer.

FIG. 7 is a front view of another dispensing well, dispensing well 110, which may be used in the device of applicant's patent. Referring to FIG. 7, it will be seen that dispensing well 110 is comprised of input port 112, (from which fluid from line 46 [see FIG. 1] may be passed), orifices 36, and outer housing 114. Absorbent material 116 is disposed between the input port and the outer housing of the dispensing well 10.

Referring to FIG. 8, it will be seen that the deodorant fluid flows in the direction of arrows 118, 120, and 122 through orifices 124 and 126 and into chamber 128. The absorbent material, indicated by the shaded lines in FIG. 8, is disposed between the inner tube 130 and the interior walls of the outer housing. In the embodiment shown, no orifice 124 or 126 exists near the bottom of inner tube 130 to allow deodorant fluid to accumulate to a certain extent on the bottom of the tube.

FIG. 9 is a top view of the cap 132 of dispensing well 110, Cap 132 is comprised of flange 134 which may be secured by fastening means (not shown) inserted through orifices 136 and connected to the surface of ductwork 20 (not shown).

FIG. 10 is a top view of inner core 130, with cap 132 removed, showing inner core 130 disposed within the housing of unit 110.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. An apparatus for dispensing odorant vapor into an air stream, comprising a reservoir for containing a volatilizable liquid, a dispensing well, a pump, and switch means for activating said pump, wherein:

(a) said dispensing well is comprised of a bottom wall and a side wall, absorbent material contiguous with said bottom wall, and at least two orifices in said side wall;

(b) said pump is comprised of a fluid inlet connected to said reservoir, and a fluid outlet connected to said dispensing well; and (c) said switch means is electrically connected to said pump and is comprised of means for causing an electrical signal to be transmitted to said pump.

2. The apparatus as recited in claim 1, wherein said pump is operatively connected to an electric motor.

3. The apparatus as recited in claim 2, wherein said switch means is electrically connected to said electric motor and is comprised of manual means for causing an electrical signal to be transmitted to said electric motor.

4. The apparatus as recited in claim 3, wherein said pump is a vacuum pump.

5. The apparatus as recited in claim 3, further comprising an electrical timer electrically connected to said electric motor.

6. The apparatus as recited in claim 3, wherein said dispensing well is constructed of plastic.

7. The apparatus as recited in claim 3, wherein said electric motor is operatively connected to a fan.

* * * * *